United States Patent [19]
de Costa et al.

[11] Patent Number: 5,571,832
[45] Date of Patent: Nov. 5, 1996

[54] NITROGEN-CONTAINING CYCLOHETERO ALKYLAMINO ARYL DERIVATIVES FOR CNS DISORDERS

[75] Inventors: Brian R. de Costa, Rockville; Wayne D. Bowen; Xiao-Shu He, both of Derwood, all of Md.; Lilian Radesca, Newark, Del.; Kenner C. Rice, Bethesda, Md.

[73] Assignee: The United States of America as represented by the Department of Health and Human Services, Washington, D.C.

[21] Appl. No.: 261,796

[22] Filed: Jun. 20, 1994

Related U.S. Application Data

[63] Continuation of Ser. No. 976,585, Nov. 13, 1992, abandoned.

[51] Int. Cl.$^6$ .................. A61K 31/40; C07D 207/08; C07D 207/12; C07D 207/46
[52] U.S. Cl. .................. 514/408; 514/423; 514/424; 514/428; 514/429; 548/530; 548/531; 548/539; 548/541; 548/542; 548/543; 548/550; 548/551; 548/556; 548/566; 548/567
[58] Field of Search .................. 548/566, 530, 548/567, 531, 539, 541, 542, 543, 550, 551, 556; 514/408, 423, 428, 424, 429

[56] References Cited

U.S. PATENT DOCUMENTS

| | | | |
|---|---|---|---|
| 4,204,003 | 5/1980 | Szmuszkovicz | 424/324 |
| 4,463,013 | 7/1984 | Collins et al. | 424/274 |
| 4,801,604 | 1/1989 | Vonvoightlander et al. | 514/429 |

FOREIGN PATENT DOCUMENTS 9212128  7/1992  WIPO.

OTHER PUBLICATIONS

S. M. Rothman et al, *Annals of Neurology*, vol. 19, No. 2, 105–111 (1986).
C. Carter et al, *J. Pharm Exp. Ther.*, 247 (3), 1222–1232 (1988).
F. F. Gilman et al, *The Pharmacological Basis of Therapeutics*, 7th ed., 404, MacMillan (1985).
C. G. Parsons et al, *Neuropharm.*, 25(2), 217–220 (1986).
W. Lason et al, *Brain Res.*, 482, 333–339 (1989).
B. R. de Costa et al, *J. Med. Chem.*, 32(8), 1996–2002 (1989).
Long et al, *Soc. Neurosci. Abs.* 16, 1122, abs 461.4 (1990).
P. C. Contreras et al, *Brain Res.*, 546, 79–82 (1991).
Scopes et al, *J. Med. Chem.*, 35, 490–501 (1992).
B. R. de Costa et al, *J. Med. Chem.*, 35(1), 38–47 (1992).
L. Radesca et al., *J. Med. Chem.*, 34 (10), 3058–65 (1991).
Derwent Abstract of WO/92128, 23 Jul. 1992.
Giuseppe Giardina, *Biosistemi Come Targets Farmacologici, Recettori Peptidergici*, Analgesici Oppioidi Kappa: Sintesi E Relazioni Struttura–Attivita' Di Piperidine Sostituite, pp. 21–63 (Sep., 1992).
David Rees, *Biosistemi Come Targets Farmacologici, Recettori Peptidergici*, Synthesis & Biological Activity of Kappa–Opioid Agonists Leading to the Selection of CI–977 (Enadoline) for Clinical Investigation, pp. 65–101 (Sep., 1992).
G. Ronsisvalle, *Biosistemi Come Targets Farmacologici, Recettori Peptidergici*, Requisiti Strutturali Per I Liganti Oppioidi: E' Possibile Modulare La Selecttivita'?, pp. 102–133 (Sep., 1992).
Pontecorvo et al, *Brain Res. Bull.*, 26, 461–65 (1991).

*Primary Examiner*—Phyllis G. Spivack
*Attorney, Agent, or Firm*—Leydig, Voit & Mayer, Ltd.

[57] ABSTRACT

Compounds comprising a pyrrolidinyl ring are disclosed for use in the treatment of cerebral ischemia.

12 Claims, No Drawings

NITROGEN-CONTAINING CYCLOHETERO ALKYLAMINO ARYL DERIVATIVES FOR CNS DISORDERS

This is a Continuation of application Ser. No. 07/976,585 filed Nov. 13, 1992, now abandoned.

FIELD OF THE INVENTION

This invention is in the field of clinical neurology and relates specifically to a class of therapeutically useful compounds, compositions and methods for treatment of Central Nervous System (CNS) dysfunctions, neurotoxic damage, or neurodegenerative diseases. For example, these compounds are particularly useful for treating neurotoxic injury which follows periods of hypoxia, anoxia or ischemia associated with stroke, cardiac arrest or perinatal asphyxia. These compounds are also useful as antipsychotics and anticonvulsives.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman and J. W. Olney, "Glutamate and the Pathophysiology of Hypoxia—Ischemic Brain Damage;" *Annals of Neurology*, vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with hypoxia, anoxia, or ischemia caused by stroke, cardiac arrest or perinatal asphyxia.

It is known that compounds of various structures, such aminophosphonovalerate derivatives and piperidine dicarboxylate derivatives, may act as competitive antagonists at the NMDA receptor. Certain piperidineethanol derivatives, such as ifenprodil and 1-(4-chlorophenyl)-2-[1-(4-fluorophenyl)piperidinyl]ethanol, which are known anti-ischemic agents, have been found to be non-competitive NMDA receptor antagonists [C. Carter et al, *J. Pharm Exp. Ther.*, 247 (3), 1222–1232 (1988)].

There are many classes of compounds known for treatment of psychotic disorders. For example, current therapeutic treatments for psychoses use compounds classifiable as phenothiazine-thioxanthenes, as phenylbutylpiperidines and also as certain alkaloids. An example of a phenylbutylpiperidine compound of current use in psychotic treatment therapy is haloperidol [A. F. Gilman et al, *The Pharmacological Basis of Therapeutics*, 7th Edn., p. 404, MacMillan (1985)].

Certain nitrogen-containing cyclohetero cycloalkylaminoaryl compounds are known for pharmaceutical purposes. For example, U.S. Pat. No. 4,204,003 to Szmuszkovicz describes N-(2-aminocyclopentyl)-N-alkanoylanilides as antidepressant agents.

Certain aminocycloaliphatic benzamides have been described for various uses. For example, U.S. Pat. No. 4,463,013 to Collins et al describes aminocyclohexylbenzamides for use as diuretic agents. The compound (±)-trans-3,4-dichloro-N-methyl-N-[2-(1-pyrrolidinyl)cyclohexyl]benzene-acetamide has been evaluated for its selectivity as an amino acid antagonist [C. G. Parsons et al, *Neuropharm.*, 25(2), 217–220 (1986)]. This same compound has been evaluated for its neuroprotective activity against kainate-induced toxicity [W. Lason et al, *Brain Res.*, 482, 333–339 (1989)]. U.S. Pat. No. 4,801,604 to Vonvoightlander et al describes certain cis-N-(2-aminocycloaliphatic)benzamides as anticonvulsants including, specifically, the compound cis-3,4-dichloro-N-methyl-N-[2-(1-pyrrolidinyl)cyclohexyl]benzamide. These benzeneacetamide derivatives, such as trans-3,4-dichloro-N-methyl-N-[2-(1-pyrrolidinyl)cyclohexyl]benzeneacetamide, have been described as a highly selective ligand for kappa opioid receptors. The cis isomers of 3,4-dichloro-N-methyl-N-[2-(1-pyrrolidinyl)cyclohexyl]benzeneacetamide were identified to be potent and selective sigma ligands [B. R. de Costa et al, *J. Med. Chem.*, 32(8), 1996–2002 (1989)]. Further structure activity studies with these compounds resulted in the identification of (+)- and (−)-cis-N-[3,4-dichlorophenylethyl]-N-methyl-2-(1-pyrrolidinyl)cyclohexylamines as extremely potent and selective ligands for the sigma receptor. These (Contreras et al, *Brain RES.*) and related (ethylenediamines) compounds (Long et al, INRC abstract) were found to be effective as protective agents for the damaging effects of ischemia and stroke in two different models of ischemia. See, for example, J. G. Long; F. C. Torella; K. C. Rice; B. R. de Costa: Selective Sigma ligands protect against dynorphin A-induced spinal cord injury in rats, *Soc. Neurosci. Abs.*, 16, 1122, (1990), abs 461.4; P. C. Contreras; D. M. Ragan; M. E. Bremer; T. H. Lanthorn; N. M. Gray; S. Iyengar; A. E. Jacobson; K. C. Rice; B. R. de Costa: Evaluation of 450488H Analogs for antiischemic activity in the gerbil, *Brain Res.*, 546, 79–82, (1991). Since these initial findings, neuroprotective acitivity has been identified among certain other high affinity sigma ligands. It is likely that the protective effects of these and related compounds is mediated through their interaction with the sigma receptor. Scopes et al., *J. Med. Chem.*, 35, 490–501 (1992) describe certain 2-[(alkylamino)methyl]-piperidines. In particular, 1-[(3,4-dichlorophenyl)acetyl]-2[(alkylamino)methyl]piperidiens are described as having activities as kappa opoid receptor agonists.

DESCRIPTION OF THE INVENTION

Treatment of CNS disorders and diseases such as cerebral ischemia, psychotic disorders, convulsions and parkinsonism, as well as prevention of neurotoxic damage and neurodegenerative diseases, may be accomplished by administration of a therapeutically-effective amount of a compound of Formula I:

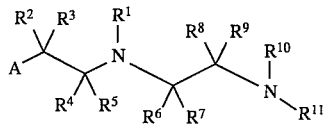

(I)

wherein each of $R^1$, $R^{10}$ and $R^{11}$ is selected from hydrido, alkyl, cycloalkyl, hydroxyalkyl, haloalkyl, cycloalkylalkyl, alkoxyalkyl, aralkyl, aryl, alkenylalkyl, alkynylalkyl, carboxyalkyl, alkanoyl, alkylsulfinyl, alkylsulfonyl, arylsulfinyl and arylsulfonyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein each of $R^4$ through $R^9$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein $R^2$ and $R^3$ may be taken together to form oxo; wherein $R^4$ and $R^5$ may be taken together to form oxo; wherein $R^6$ and $R^7$ may be taken together to form oxo; wherein $R^8$ and $R^9$ may be taken together to form oxo; wherein one of $R^{10}$ or $R^{11}$ together with one of $R^6$ or $R^7$, or together with one of $R^8$ or $R^9$, form a heterocyclic ring moiety which includes the nitrogen atom to which $R^{10}$ and $R^{11}$ are attached, said ring moiety having from five to ten ring members; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically-acceptable salt thereof.

A preferred family of compounds of Formula I consists of those compounds wherein each of $R^1$, $R^{10}$ and $R^{11}$ is selected from hydrido, alkyl, cycloalkyl, hydroxyalkyl, haloalkyl, cycloalkylalkyl, alkoxyalkyl, aralkyl, aryl, alkenylalkyl, alkynylalkyl and carboxyalkyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy and cyanoalkyl; wherein each of $R^4$ through $R^9$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein $R^4$ and $R^5$ may be taken together to form oxo; wherein $R^6$ and $R^7$ may be taken together to form oxo; wherein $R^8$ and $R^9$ may be taken together to form oxo; wherein one of $R^{10}$ and $R^{11}$ together with one of $R^6$ and $R^7$, or together with one of $R^8$ and $R^9$, form a heterocyclic ring moiety which includes the nitrogen atom to which $R^{10}$ and $R^{11}$ are attached, said ring moiety having from five to ten ring members; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically acceptable salt thereof.

A more preferred family of compounds within Formula I consists of those compounds wherein each of $R^1$, $R^{10}$ and $R^{11}$ is selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenylloweralkyl, loweralkynylloweralkyl and carboxyloweralkyl; wherein each of $R^2$ and $R^3$ is independently selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenyl, loweralkynyl, loweralkenylloweralkyl, loweralkynylloweralkyl, carboxyloweralkyl, loweralkanoyl, loweralkoxycarbonyl, carboxy and cyanoloweralkyl; wherein each of $R^4$ through $R^9$ is independently selected from hydrido, loweralkyl, cycloalkyl of three to about eight carbon atoms, cycloalkylalkyl of four to about eight carbon atoms, phenylloweralkyl, phenyl, loweralkoxyloweralkyl, haloloweralkyl, hydroxyloweralkyl, carboxy, carboxyloweralkyl, loweralkanoyl, loweralkenyl and loweralkynyl; wherein $R^4$ and $R^5$ may be taken together to form oxo; wherein $R^6$ and $R^7$ may be taken together to form oxo; wherein $R^8$ and $R^9$ may be taken together to form oxo; wherein one of $R^{10}$ and $R^{11}$ together with one of $R^6$ and $R^7$, or together with one of $R^8$ and $R^9$, form a heterocyclic ring moiety which includes the nitrogen atom to which $R^{10}$ and $R^{11}$ are attached, said ring moiety having from five to ten ring members; wherein A is selected from phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino, phenylloweralkylamino, natphthylloweralkylamino, heteroaralkylamino, phenylthio, naphthylthio, heteroarylthio, phenylloweralkylthio and heteroarylloweralkylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

A more highly preferred family of compounds of Formula I consists of those compounds wherein each of $R^1$, $R^{10}$ and $R^{11}$ is selected from hydrido, loweralkyl, cycloalkyl of three to about eight carbon atoms, cycloalkylalkyl of four to about eight carbon atoms, benzyl, phenyl, loweralkenylloweralkyl and loweralkynylloweralkyl; wherein each of $R^2$ and $R^3$ is independently selected from hydrido, loweralkyl, cycloalkyl of three to about eight carbon atoms, cycloalkylalkyl of four to about eight carbon atoms, benzyl, phenyl, loweralkenyl, loweralkynyl, loweralkenylloweralkyl, loweralkynylloweralkyl, loweralkanoyl and loweralkoxycarbonyl; wherein each of $R^4$ through $R^9$ is independently selected from hydrido, loweralkyl, cycloalkyl of three to about eight carbon atoms, cycloalkylalkyl of four to about eight carbon atoms, benzyl, phenyl, loweralkoxyloweralkyl, haloloweralkyl, hydroxyloweralkyl, loweralkanoyl, loweralkenyl and loweralkynyl; wherein $R^4$ and $R^5$ may be taken together to form oxo; wherein $R^6$ and $R^7$ may be taken together to form oxo; wherein $R^8$ and $R^9$ may be taken together to form oxo; wherein one of $R^{10}$ and $R^{11}$ together with one of $R^6$ and $R^7$, or together with one of $R^8$ and $R^9$, form a heterocyclic ring moiety which includes the nitrogen atom to which $R^{10}$ and $R^{11}$ are attached, said ring moiety having from five to ten ring members; wherein A is selected from phenyl, naphthyl, thienyl, phenoxy, benzyloxy, naphthyloxy, thiophenoxy, phenylamino, benzylamino, naphthylamino, phenylthio, benzylthio and naphthylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

A preferred sub-class of compounds within Formula I are compounds represented by Formula II:

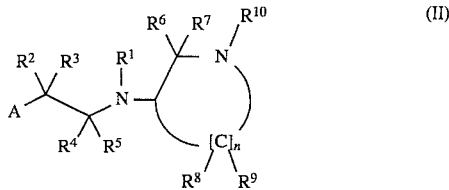

(II)

wherein each of $R^1$ and $R^{10}$ is selected from hydrido, alkyl, cycloalkyl, hydroxyalkyl, haloalkyl, cycloalkylalkyl, alkoxyalkyl, aralkyl, aryl, alkenylalkyl, alkynylalkyl, carboxyalkyl, alkanoyl, alkylsulfinyl, alkylsulfonyl, arylsulfinyl and arylsulfonyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein each of $R^4$ through $R^9$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein $R^2$ and $R^3$ may be taken together to form oxo; wherein $R^4$ and $R^5$ may be taken together to form oxo; wherein $R^6$ and $R^7$ may be taken together to form oxo; wherein $R^8$ and $R^9$ may be taken together to form oxo; wherein n is an integer of from 2 to 7; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically-acceptable salt thereof.

A preferred family of compounds within Formula II are those compounds wherein $R^1$ and $R^{10}$ is selected from hydrido, alkyl, cycloalkyl, hydroxyalkyl, haloalkyl, cycloalkylalkyl, alkoxyalkyl, aralkyl, aryl, alkenylalkyl, alkynylalkyl and carboxyalkyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy and cyanoalkyl; wherein each of $R^4$ through $R^9$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein $R^4$ and $R^5$ may be taken together to form oxo; wherein $R^6$ and $R^7$ may be taken together to form oxo; wherein $R^8$ and $R^9$ may be taken together to form oxo; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically acceptable salt thereof.

A more preferred family of compounds within Formula II are those compounds wherein $R^1$ and $R^{10}$ is selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenylloweralkyl, loweralkynylloweralkyl and carboxyloweralkyl; wherein each of $R^2$ and $R^3$ is independently selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenyl, loweralkynyl, loweralkenylloweralkyl, loweralkynylloweralkyl, carboxyloweralkyl, loweralkanoyl, loweralkoxycarbonyl, carboxy and cyanoloweralkyl; wherein each of $R^4$ through $R^9$ is independently selected from hydrido, loweralkyl, cycloalkyl of three to about eight carbon atoms, cycloalkylalkyl of four to about eight carbon atoms, phenylloweralkyl, phenyl, loweralkoxyloweralkyl, haloloweralkyl, hydroxyloweralkyl, carboxy, carboxyloweralkyl, loweralkanoyl, loweralkenyl and loweralkynyl; wherein $R^4$ and $R^5$ may be taken together to form oxo; wherein $R^6$ and $R^7$ may be taken together to form oxo; wherein $R^8$ and $R^9$ may be taken together to form oxo; wherein A is selected from phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino, phenylloweralkylamino, naphthylloweralkylamino, heteroaralkylamino, phenylthio, naphthylthio, heteroarylthio, phenylloweralkylthio and heteroarylloweralkylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenyloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

A more highly preferred family of compounds within Formula II are those compounds wherein $R^1$ and $R^{10}$ is selected from hydrido, loweralkyl, cycloalkyl of three to about eight carbon atoms, cycloalkylalkyl of four to about eight carbon atoms, benzyl, phenyl, loweralkenylloweralkyl and loweralkynylloweralkyl; wherein each of $R^2$ and $R^3$ is independently selected from hydrido, loweralkyl, cycloalkyl of three to about eight carbon atoms, cycloalkylalkyl of four to about eight carbon atoms, benzyl, phenyl, loweralkenyl, loweralkynyl, loweralkenylloweralkyl, loweralkynylloweralkyl, loweralkanoyl and loweralkoxycarbonyl; wherein each of $R^4$ through $R^9$ is independently selected from hydrido, loweralkyl, cycloalkyl of three to about eight carbon atoms,, cycloalkylalkyl of four to about eight carbon atoms, benzyl, phenyl, loweralkoxyloweralkyl, haloloweralkyl, hydroxyloweralkyl, loweralkanoyl, loweralkenyl and loweralkynyl; wherein $R^4$ and $R^5$ may be taken together to form oxo; wherein $R^6$ and $R^7$ may be taken together to form oxo; wherein $R^8$ and $R^9$ may be taken together to form oxo; wherein A is selected from phenyl, naphthyl, thienyl, phenoxy, benzyloxy, naphthyloxy, thiophenoxy, phenylamino, benzylamino, naphthylamino, phenylthio, benzylthio and naphthylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

Compounds of particular interest which fall within the scope of Formula II include:

3-[N-(3,4-dichlorophenyl)ethyl]-N-(methyl)amino]-1-(methyl)piperidine
3-[N-(3,4-dichlorophenyl)ethyl]-N-(methyl)amino]-1-(methyl)homopiperidine
3-[N-(3,4-dichlorophenyl)ethyl]-N-(methyl)amino]-1-(methyl)pyrrolidine
3-[N-(3-benzothienyl)ethyl]-N-(methyl)amino]-1-(methyl)piperidine
3-[N-(3-benzothienyl)ethyl]-N-(methyl)amino]-1-(methyl)homopiperidine
3-[N-(3-benzothienyl)ethyl]-N-(methyl)amino]-1-(methyl)pyrrolidine
3-[N-(2-[2-napthyl]ethyl)]-N-(methyl)amino]-1-(methyl)piperidine
3-[N-(2-[2-napthyl]ethyl)]-N-(methyl)amino]-1-(methyl)homopiperidine
3-[N-(2-[2-napthyl]ethyl)]-N-(methyl)amino]-1-(methyl)pyrrolidine Another preferred sub-class of compounds within Formula I are those compounds represented by Formula III:

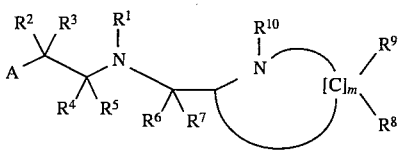

(III)

wherein each of $R^1$ and $R^{10}$ is selected from hydrido, alkyl, cycloalkyl, hydroxyalkyl, haloalkyl, cycloalkylalkyl, alkoxyalkyl, aralkyl, aryl, alkenylalkyl, alkynylalkyl, carboxyalkyl, alkanoyl, alkylsulfinyl, alkylsulfonyl, arylsulfinyl and arylsulfonyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl and arylsulfonyl; wherein each of $R^4$ through $R^9$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein $R^2$ and $R^3$ may be taken together to form oxo; wherein $R^4$ and $R^5$ may be taken together to form oxo; wherein $R^6$ and $R^7$ may be taken together to form oxo; wherein $R^8$ and $R^9$ may be taken together to form oxo; wherein m is an integer of from 3 to 8; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically-acceptable salt thereof.

A preferred family of compounds within Formula III are those compounds wherein each of $R^1$ and $R^{10}$ is selected from hydrido, alkyl, cycloalkyl, hydroxyalkyl, haloalkyl, cycloalkylalkyl, alkoxyalkyl, aralkyl, aryl, alkenylalkyl, alkynylalkyl and carboxyalkyl; wherein each of $R^2$ and $R^3$ is independently selected from hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy and cyanoalkyl; wherein each of $R^4$ through $R^9$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl; wherein $R^4$ and $R^5$ may be taken together to form oxo; wherein $R^6$ and $R^7$ may be taken together to form oxo; wherein $R^8$ and $R^9$ may be taken together to form oxo; wherein A is selected from aryl, heteroaryl, aryloxy, heteroaryloxy, aralkoxy, heteroaralkoxy, arylamino, heteroarylamino, aralkylamino, heteroaralkylamino, arylthio, heteroarylthio, aralkylthio and heteroaralkylthio; wherein any of the foregoing A groups can be further substituted with one or more substituents independently selected from hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically acceptable salt thereof.

A more preferred family of compounds within Formula III are those compounds wherein each of $R^1$ and $R^{10}$ is selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenylloweralkyl, loweralkynylloweralkyl and carboxyloweralkyl; wherein each of $R^2$ and $R^3$ is independently selected from hydrido, loweralkyl, cycloalkyl of three to about eight carbon atoms, hydroxyloweralkyl, haloloweralkyl, cycloalkylalkyl of four to about eight carbon atoms, loweralkoxyloweralkyl, phenylloweralkyl, phenyl, loweralkenyl, loweralkynyl, loweralkenylloweralkyl, loweralkynylloweralkyl, carboxyloweralkyl, loweralkanoyl, loweralkoxycarbonyl, carboxy and cyanoloweralkyl; wherein each of $R^4$ through $R^9$ is independently selected from hydrido, loweralkyl, cycloalkyl of three to about eight carbon atoms, cycloalkylalkyl of four to about eight carbon atoms, phenylloweralkyl, phenyl, loweralkoxyloweralkyl, haloloweralkyl, hydroxyloweralkyl, carboxy, carboxyloweralkyl, loweralkanoyl, loweralkenyl and loweralkynyl; wherein $R^4$ and $R^5$ may be taken together to form oxo; wherein $R^6$ and $R^7$ may be taken together to form oxo; wherein $R^8$ and $R^9$ may be taken together to form oxo; wherein A is selected from phenyl, naphthyl, heteroaryl, phenoxy, naphthyloxy, heteroaryloxy, phenylloweralkoxy, naphthylloweralkoxy, heteroarylloweralkoxy, phenylamino, naphthylamino, heteroarylamino, phenylloweralkylamino, naphthylloweralkylamino, heteroaralkylamino, phenylthio, naphthylthio, heteroarylthio, phenylloweralkylthio and heteroarylloweralkylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, phenylloweralkyl, phenyl, loweralkoxy, phenoxy, phenylloweralkoxy, loweralkoxyloweralkyl, halo, haloloweralkyl, hydroxyloweralkyl, cyano, amino, monoloweralkylamino, diloweralkylamino, carboxy, carboxyloweralkyl, loweralkanoyl, loweralkenyl and loweralkynyl; or a pharmaceutically acceptable salt thereof.

A more highly preferred family of compounds, within Formula III are those compounds wherein each of $R^1$ and $R^{10}$ is selected from hydrido, loweralkyl, cycloalkyl of three to about eight carbon atoms, cycloalkylalkyl of four to about eight carbon atoms, benzyl, phenyl, loweralkenylloweralkyl and loweralkynylloweralkyl; wherein each of $R^2$ and $R^3$ is independently selected from hydrido, loweralkyl, cycloalkyl of three to about eight carbon atoms, cycloalkylalkyl of four to about eight carbon atoms, benzyl, phenyl, loweralkenyl, loweralkynyl, loweralkenylloweralkyl, loweralkynylloweralkyl, loweralkanoyl and loweralkoxycarbonyl; wherein each of $R^4$ through $R^9$ is independently selected from hydrido, loweralkyl, cycloalkyl of three to about eight carbon atoms, cycloalkylalkyl of four to about eight carbon atoms, benzyl, phenyl, loweralkoxyloweralkyl, haloloweralkyl, hydroxyloweralkyl, loweralkanoyl, loweralkenyl and loweralkynyl; wherein $R^4$ and $R^5$ may be taken together to form oxo; wherein $R^6$ and $R^7$ may be taken together to form oxo; wherein $R^8$ and $R^9$ may be taken together to form oxo; wherein A is selected from phenyl, naphthyl, thienyl, phenoxy, benzyloxy, naphthyloxy, thiophenoxy, phenylamino, benzylamino, naphthylamino, phenylthio, benzylthio and naphthylthio; wherein any of the foregoing A groups can be further substituted with one or more substituents independently selected from hydrido, hydroxy, loweralkyl, cycloalkyl of three to about eight carbon atoms, cycloalkylalkyl of four to about eight carbon atoms, loweralkoxy, loweralkoxyloweralkyl, halo, haloloweralkyl, hydroxyloweralkyl, amino, monoloweralkylamino, diloweralkylamino, loweralkanoyl, loweralkenyl and loweralkynyl; or a pharmaceutically acceptable salt thereof.

Compounds of particular interest which fall within the scope of Formula III include:

2-[N-[2-(3,4-dichlorophenyl)ethyl]-N-(methyl)aminoethyl]-1-(methyl)piperidine

2-[N-[2-(3,4-dichlorophenyl)ethyl]-N-(methyl)aminoethyl]-1-(methyl)homopiperidine 2-[N-[2-(3,4-dichlorophenyl)ethyl]-N-(methyl)aminoethyl]-1(methyl)pyrrolidine 2-[N-(3-benzothienyl)ethyl]-N-(methyl)aminoethyl]-1-(methyl)piperidine 2-[N-(3-benzothienyl)ethyl]-N-(methyl)aminoethyl]-1-(methyl)homopiperidine 2-[N-(3-benzothienyl)ethyl]-N-(methyl)aminoethyl]-1-(methyl)pyrrolidine 2-[N-(2-[2-napthyl]ethyl)]-N-(methyl)aminoethyl]-1-(methyl)piperidine 2-[N-(2-[2-napthyl]ethyl)]-N-(methyl)aminoethyl]-1-(methyl)homopiperidine 2-[N-(2-[2-napthyl]ethyl)]-N-(methyl)aminoethyl]-1-(methyl)pyrrolidine 2-[N-(3,4-dichlorophenyl)ethyl]-N-(methyl)aminoethyl]-1-(ethyl)piperidine 2-[N-(3,4-dichlorophenyl)ethyl]-N-(methyl)aminoethyl]-1-(ethyl)homopiperidine 2-[N-(3,4-dichlorophenyl)ethyl]-N-(methyl)aminoethyl]-1-(ethyl)pyrrolidine 2-[N-(3-benzothienyl)ethyl]-N-(methyl)aminoethyl]-1-(ethyl)piperidine 2-[N-(3-benzothienyl)ethyl]-N-(methyl)aminoethyl]-1-(ethyl)homopiperidine 2-[N-(3-benzothienyl)ethyl]-N-(methyl)aminoethyl]-1-(ethyl)pyrrolidine 2-[N-(2-[2-naphthyl]ethyl)]-N-(methyl)aminoethyl]-1-(ethyl)piperidine 2-[N-(2-[2-naphthyl]ethyl)]-N-(methyl)aminoethyl]-1-(ethyl)homopiperidine 2-[N-(2-[2-naphthyl]ethyl)]-N-(methyl)aminoethyl]-1-(ethyl)pyrrolidine 2-[N-(3,4-dichlorophenylethyl)aminomethyl]-1-(ethyl)pyrrolidine 2-[N-(3,4-dichlorophenylethyl)aminomethyl]-1-(ethyl)piperidine 2-[N-(3,4-dichlorophenylethyl)aminomethyl]-1-(ethyl)homopiperidine 2-[N-(3-benxothienyl)ethyl)aminomethyl]-1-(ethyl)pyrrolidine 2-[N-(3-benxothienyl)ethyl)aminomethyl]-1-(ethyl)piperidine 2-[N-(3-benxothienyl)ethyl)aminomethyl]- 1-(ethyl)homopiperidine 2-[N-(2-[2-naphthyl]ethyl)aminomethyl]-1-(ethyl)pyrrolidine 2-[N-(2-[2-naphthyl]ethyl)aminomethyl]-1-(ethyl)piperidine 2-[N-(2-[2-naphthyl]ethyl)aminomethyl]-1-(ethyl)homopiperidine The term "hydrido" denotes a single hydrogen atom (H). This hydrido group may be attached, for example, to an oxygen atom to form a hydroxyl group; or as another example, two hydrido groups may be attached to a carbon atom to form a divalent —$CH_2$— group, that is, a "methylene" group; or as another example, one hydrido group may be attached to a carbon atom to form a trivalent —CH< group. Where the term "alkyl" is used, either alone or within other terms such as "haloalkyl" and "hydroxyalkyl", the term "alkyl" embraces linear or branched radicals having one to about twenty carbon atoms or, preferably, one to about ten carbon atoms. More preferred alkyl radicals are "lower alkyl" radicals having one to about five carbon atoms. The term "cycloalkyl" embraces cyclic radicals having three to about six carbon atoms, such as cyclopropyl and cyclobutyl. The term "haloalkyl" embraces radicals wherein any one or more of the alkyl carbon atoms is substituted with one or more halo groups, preferable selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. An example of a polyhaloalkyl is a trifluoromethyl group. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferable two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. The term "alkylene chain" describes a chain of two to six methylene ($-CH_2-$) groups which may form a cyclic structure with or without a hetero atom in the cyclic structure.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neo-pentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within the family of compounds of Formula I are the tautomeric forms of the described compounds, isomeric forms including enantiomers and diastereoisomers, and the pharmaceutically-acceptable salts thereof. The term "pharmaceutically-acceptable salts" embraces salts commonly used to form alkali metal salts and to form addition salts of free acids or free bases. Since the compounds of Formulas I-III contain basic nitrogen atoms, such salts are typically acid addition salts. The phrase "pharmaceutically-acceptable salts" is not intended to embrace quaternary ammonium salts. The nature of the salt is not critical, provided that it is pharmaceutically acceptable, and acids which may be employed to form salts are, of course, well known to those skilled in the art. Examples of acids which may be employed to form pharmaceutically acceptable acid addition salts include such inorganic acids as hydrochloric acid, sulfuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding compound of Formulas I-III.

General Synthetic Procedures

Compounds of Formula I may be prepared in accordance with the following generic procedures. The following generic procedure illustrates specifically procedures for preparing compounds of Formula II.

Step 1

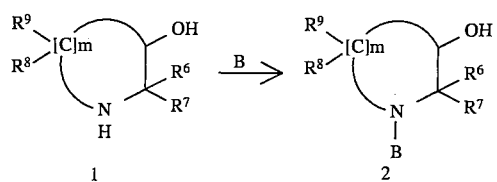

wherein $R^6$ through $R^9$, and m are as defined previously; and wherein B represents a carbamate-type protecting group such as t-butyloxycarbonyl or benzyloxycarbonyl.

A process for preparing the compounds of the invention starts with hydroxy-substituted cycloaminoalkyl compounds of general structure 1 where $R^6$ through $R^9$, and m have the value assigned previously. An example of a compound within the general structure 1 is 3-hydroxypiperidine. The amino group of 1 is protected employing carbamate-type protecting groups such as acetyl, benzoyl, t-butoxycarbonyl or benzyloxycarbonyl or other amino protecting groups familiar to those skilled in the art. This protection can be achieved by reacting the protecting group as the chloride or anhydride in organic solvents and at temperatures ranging from −60° to reflux of the reaction mixture.

Step 2

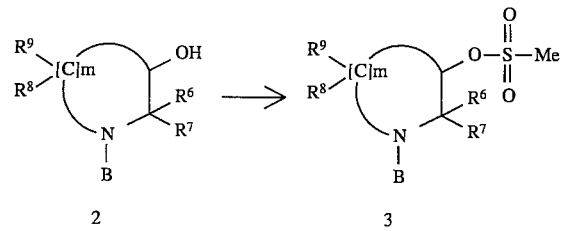

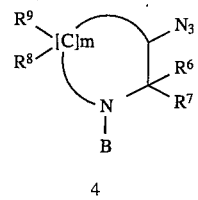

wherein B, $R^6$, $R^7$, $R^8$, $R^9$ and m are as defined previously.

In the second step of the process, the hydroxyl group of the N-protected compounds of general structure 2 are converted to the corresponding azides of general structure 4 through the corresponding methanesulfonate ester of general structure t where B, $R^6$, $R^7$, $R^8$, $R^9$ and m are as defined previously. The compounds can be combined neat or in a variety of solvents such as tetrahydrofuran. For example, treatment of a stirred solution of 2 in dry THF at ambient temperature containing triethylamine (3 molar equivalents) with methanesulfonyl chloride (1.2 molar equivalents) afforded 3. This was isolated by standard methods familiar to those skilled in the art. The methanesulfonate ester 3 was dissolved in dry DMF and heated and stirred (70° C., overnight) with excess sodium azide (3–5 molar equivalents). The product 4 was isolated by standard methods familiar to those skilled in the art. The temperature of the reaction can vary from room temperature to reflux of the reaction mixture.

Step 3

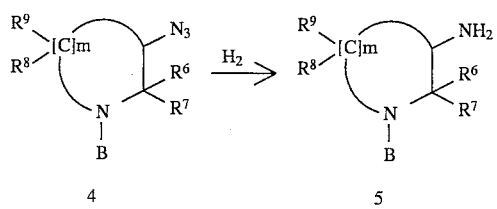

wherein B, $R^6$, $R^7$, $R^8$, $R^9$ and m are as defined previously.

In the third step of the process, azides of general structure 4 are reduced to amines of general structure 5 by employing catalytic hydrogenation, or other reducing agents familiar to those skilled in the art. This reduction can be accomplished in either protic or aprotic solvents, depending on the reducing agent of choice, and at temperatures ranging from room temperature to reflux of the reaction mixture.

Step 4

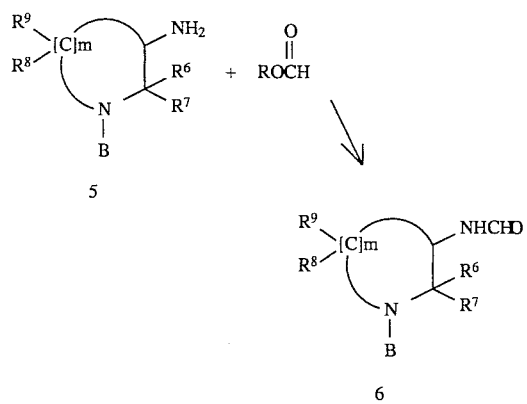

wherein B, $R^6$, $R^7$, $R^8$, $R^9$ and m are as defined previously.

In the fourth step of the process, the amines of general structure 5 are converted to amides of general structure 6 by reaction with formate ester such as $$\underset{CH_3CH_2OCH.}{\overset{O}{\|}}$$

The conversion is best achieved by mixing with the neat alkylformate. The temperature of the reaction can vary from room temperature to reflux of the reaction mixture.

Step 5

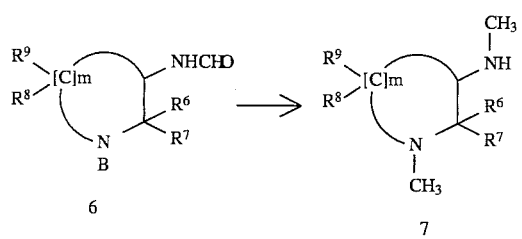

In the fifth step of the process amides of general formula 6 are converted to amines of general formula 7 by simultaneous reduction of carbamate protecting group B and the formate group. This can be accomplished utilizing a reducing agent such as for example lithium aluminum hydride, in a suitable solvent such as THF. The reaction can be conducted at a temperature ranging from room temperature to reflux of the reaction mixture.

Step 6

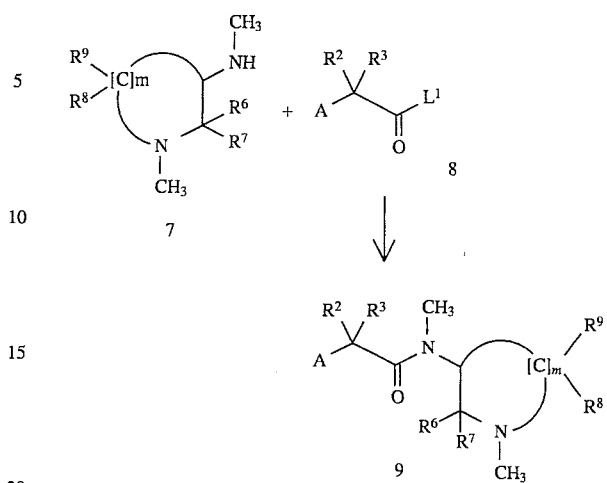

wherein A, $R^2$, $R^3$, $R^6$ through $R^9$ and m are as defined previously; and wherein $L^1$ is a good leaving group such as chloro, bromo, acyloxy, or "activated" hydroxy.

In the sixth step of the process, amines of general structure I are converted to amides of general structure 9 where A, $R^2$, and $R^3$ have the value assigned previously and $L^1$ is a good leaving group such as chloro, bromo, acyloxy, or "activated" hydroxy. The conversion can be best achieved by mixing the reagents neat or in an aprotic solvent such as tetrahydrofuran, methylene chloride, or ether in the presence of a base such as triethylamine. The reaction can be run in the absence or presence of an activating agent such as dicyclohexylcarbodiimide or phosphorus oxychloride, depending on the leaving group of choice. The temperature of the reaction can vary from 0° to reflux of the reaction mixture.

Step 7

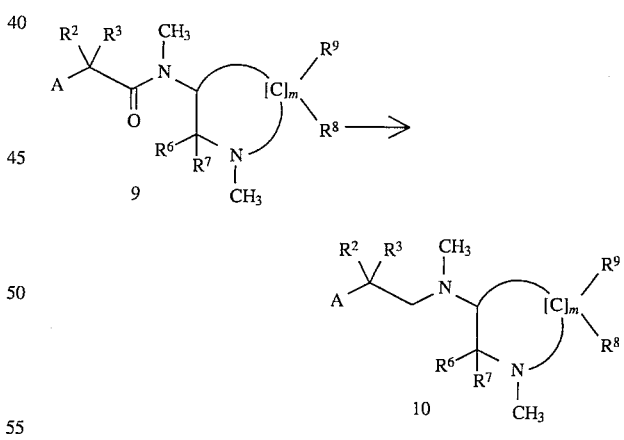

wherein A, $R^2$, $R^3$, $R^6$ through $R^9$ and m are as defined previously.

In the seventh step of the process, amides of general structure 9 are converted to amines of general structure 10 by employing reducing agents such as lithium aluminum hydride, aluminum hydride, sodium borohydride, sodium cyanoborohydride, or other reducing agents familiar to those skilled in the art. This reduction can be accomplished in either protic or aprotic solvents, depending on the reducing agent of choice, and at temperatures ranging from room temperature to reflux of the reaction mixture.

The scheme set forth below illustrates in more detail a procedure for preparing a compound of Formula II.

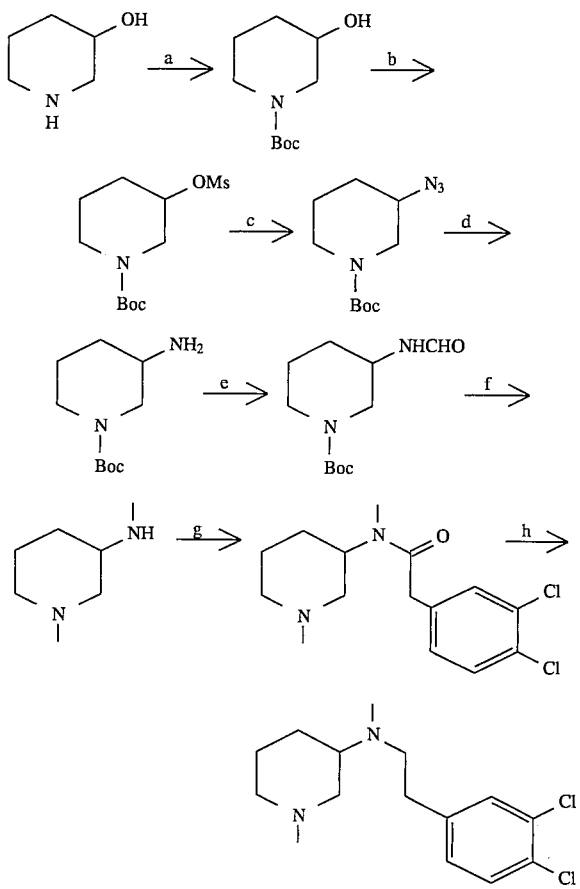

a: (Boc)$_2$O, aq NaHCO$_3$, r.t.;
b: MeSO$_3$Cl, THF, Et$_3$N;
c: NaN$_3$, DMF, 70° C.;
d: H$_2$, 10% Pd/C, MeOH—AcOH (1:1);
e: EtOCHO, reflux;
f: LiAlH$_4$, THF, reflux,
g: 3,4-dichlorophenylacetic acid, DCC, CH$_2$Cl$_2$, r.t.;
h: AlH$_3$, THF, r.t.

Compounds of Formula I may also be prepared in accordance with the following generic procedure, within which specific schemes are shown for Formula III type compounds.
Step 1

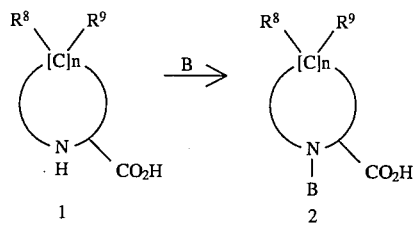

wherein R$^8$, R$^9$ and n are as defined previously; and wherein B represents a carbamate-type protecting group such as t-butyloxycarbonyl or benzyloxycarbonyl.

A process for preparing the compounds of the invention starts with carboxylic acid derivatives of cycloaminoalkyl compounds of general structure 1 where R$^8$ and R$^9$, and n have the value assigned previously. Examples of compounds within the general structure 1 are the enantiomers of proline (2-pyrrolidinecarboxylic acid) and 2-piperidinecarboxylic acid. The amino group of 1 is protected employing carbamate-type protecting groups such as t-butoxycarbonyl or benzyloxycarbonyl or other amino protecting groups familiar to those skilled in the art. This protection can be achieved by reacting the protecting group as the chloride or anhydride in organic solvents and at temperatures ranging from –60° to reflux of the reaction mixture.

Step 2

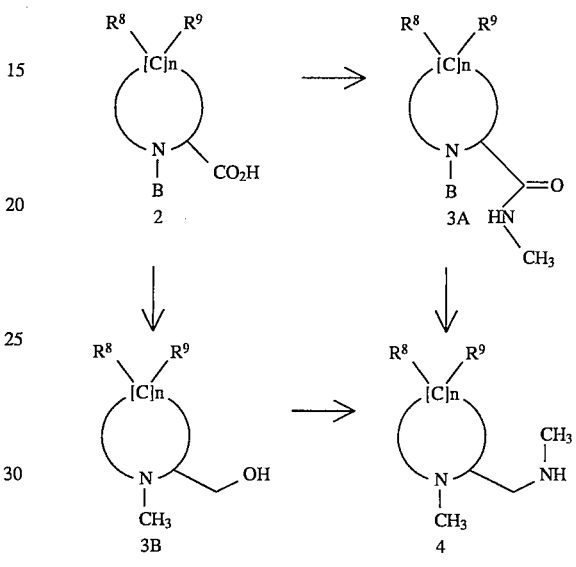

wherein B, R$^8$, R$^9$ and n are as defined previously.

In the second step of the process, compounds of the general structure 2 are converted to compounds of structure 3A by reacting 2 with an amine in the presence of isobutyl chloroformate and triethylamine.

The compounds can be combined neat or in a variety of solvents such as CHCl$_3$ tetrahydrofuran. Compounds of structure 2 can be converted to compounds of structure 3B by reducing 2 with a reducing agent such as lithium aluminum hydride. Following isolation, 3A is converted to compound 4 utilizing a reducing agent such as lithium aluminum hydride. Compounds of structure 3B are converted to, structure 4 utilizing methane sulfonyl chloride followed by treatment of the resulting methane sulfonate ester with an excess of an amine such as MeNH$_2$ (gas). The temperature of the reaction can vary from room temperature to reflux of the reaction mixture. For example, treatment of a solution of 2, 2 in CHCl$_3$ at –10° C. with Et$_3$N (excess), isobutyl chloroformate (1 molar equivalent), and methylamine (gas) (excess) afforded 3A. This was isolated by standard methods familiar to those skilled in the art. The product 3A was dissolved in trifluoroacetic acid and the solution was stirred for one hour. The product 4 was isolated by evaporation of the trifluoroacetic acid in vacuo. The temperature of the reaction can vary from room temperature to reflux of the reaction mixture.

Step 3

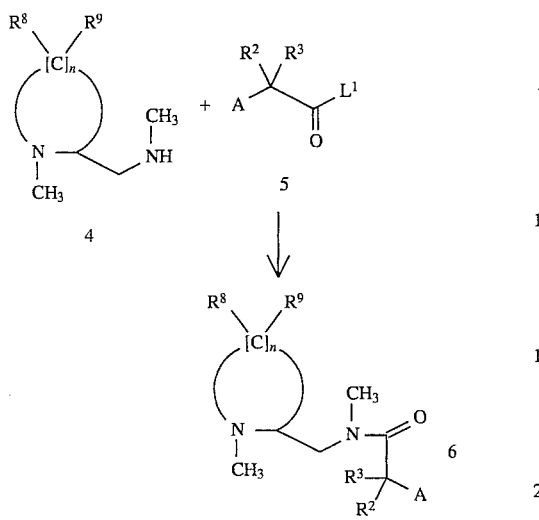

wherein A, $R^2$, $R^3$, $R^8$, $R^9$ and n are as defined previously; and wherein $L^1$ is a good leaving group such as chloro, bromo, acyloxy, or "activated" hydroxy. In the third step of the process, compounds of general structure 4 are converted to amides of general structure 6 where A, $R^2$, and $R^3$ have the value assigned previously and $L^1$ is a good leaving group such as chloro, bromo, acyloxy, or "activated" hydroxy. The conversion can be best achieved by mixing the reagents neat or in an aprotic solvent such as tetrahydrofuran, methylene chloride, or ether in the presence of a base such as triethylamine. The reaction can be run in the absence or presence of an activating agent such as dicyclohexylcarbodiimide or phosphorus oxychloride, depending on the leaving group of choice. The temperature of the reaction can vary from 0° to reflux of the reaction mixture.

Step 4

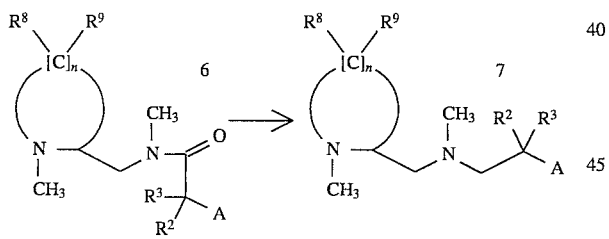

wherein A, $R^2$, $R^3$, $R^8$, $R^9$ and n are as defined previously.

In the fourth step of the process, amides of general structure f are converted to amines of general structure 7 by employing reducing agents such as lithium aluminum hydride, aluminum hydride, sodium borohydride, sodium cyanoborohydride, or other reducing agents familiar to those skilled in the art. This reduction can be accomplished in either protic or aprotic solvents, depending on the reducing agent of choice, and at temperatures ranging from room temperature to reflux of the reaction mixture.

Step 3(b)

Alternately, amines of general structure 9 can be prepared according to the following generic procedure.

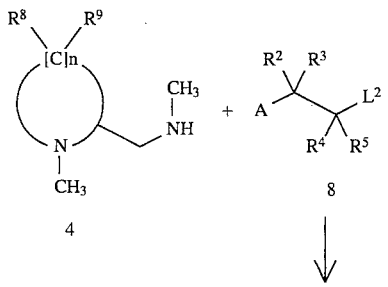

wherein A, $R^2$ through $R^9$ and n are as defined previously; and wherein $L^2$ is a good leaving group such as halogen, tosylate, mesylate, or brosylate.

Amines of general structure 9 can be alternately prepared by combining compounds of general structure 4 with compounds of general structure 8 where A, $R^2$ through $R^9$ and n have the values assigned previously and where $L^2$ is a good leaving group such as halogen, tosylate, mesylate, or brosylate. The compounds can be combined in a variety of solvents such as toluene, xylenes, dimethylformamide, hexamethylphosphoramide, or ethanol. The temperature of the reaction can vary from room temperature to reflux of the reaction mixture.

The following specific schemes illustrate the procedure for preparing Formula III compounds in more detail.

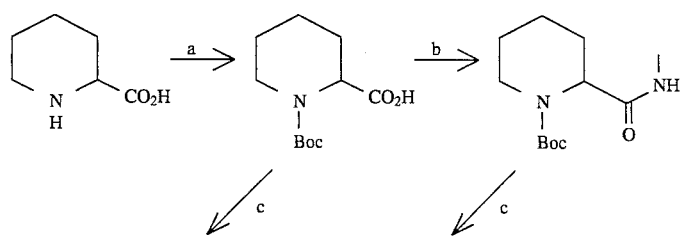

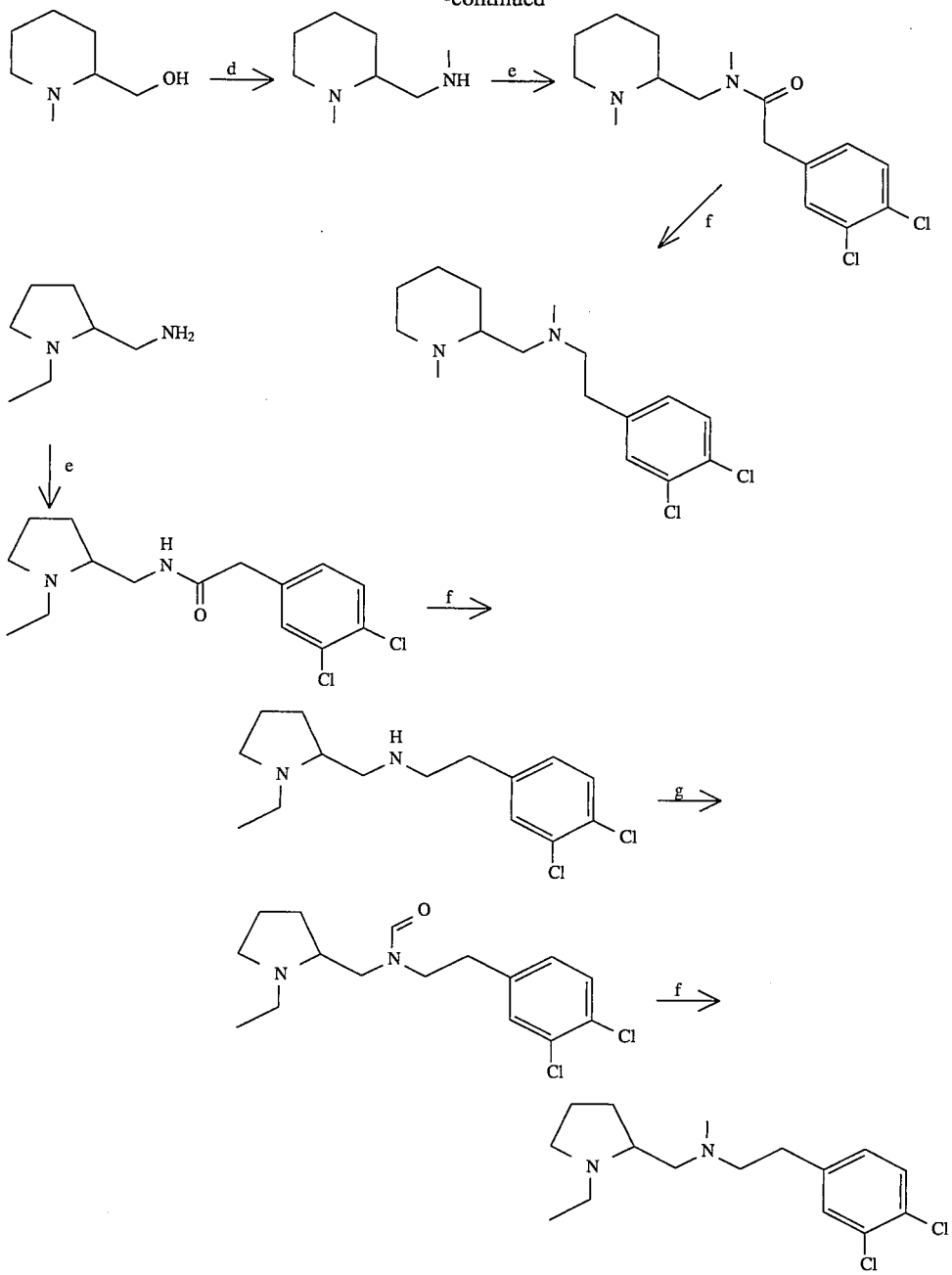

a: (Boc)$_2$O, saturated aqueous NaHCO$_3$;
b: (i) isobutyl chloroformate, Et$_3$N, CHCl$_3$, −10° C.; (ii) MeNH$_2$ (gas);
c: LiAlH$_4$, THF, reflux;
d: (i) CH$_3$SO$_2$Cl, Et$_3$N, CHCl$_3$; (ii) MeNH, (40% aqueous solution), H$_2$O, r.t.;
f: AlH$_3$, THF, r.t.;
g: EtOCHO, reflux.

The following Examples are detailed descriptions of the methods of preparation of compounds of Formula I. These detailed preparations fall within the scope of, and serve to exemplify, the above described Generic Procedures which form part of the invention. These Examples are presented for illustrative purposes only and are not intended as a restriction on the scope of the invention. All parts are by weight unless otherwise indicated. Most of the commercially available starting materials were obtained from Aldrich Chemical Company, Milwaukee, Wis.

Melting points were determined on a Thomas-Hoover capillary apparatus and are uncorrected. Elemental analyses were performed at Atlantic Microlabs, Atlanta, Ga.; where molecular formulae are indicated followed by the symbols of the elements, analyses are within ±0.4% of the theoretical values. Chemical-ionization mass spectra (CIMS) were obtained using a Finnigan 1015 mass spectrometer. Electron ionization mass spectra (EIMS) and high resolution mass measurements (HRMS) were obtained using a VG-Micro Mass 7070F mass spectrometer. $^1$H-NMR spectra were measured from CDCl$_3$ solutions using a Varian SL-300 spectrometer. Thin layer chromatography (TLC) was performed on 250 μM Analtech GHLF silica gel plates. TLC system A corresponds to CHCl$_3$—MeOH-conc. aq. NH$_3$ (90:9:1). TLC system B corresponds to CHCl₃—MeOH-conc. aq. NH₃ (80:18:2). TLC system C corresponds to EtOAc/hexanes (1:2). No attempt was made to optimize the yields. For purposes of clarity, racemic compounds are shown without prefixes.

EXAMPLE 1

1-(tert-Butoxycarbonyl)-3-(hydroxy)piperidine

To a stirred solution of 3-hydroxypiperidine (25.0 g, 247 mmol) and NaHCO₃ (62.3 g, 742 mmol, 3 eq) in water (500 mL) was added di-t-butoxydicarbonate (64.7 g, 296 mmol, 1.2 eq) and the solution was stirred for 48 h at rt. The aqueous mixture was extracted with $CH_2Cl_2$ (3×200 mL). The combined organic extract was back-washed with water (50 mL) and dried by filtration through $Na_2SO_4$. Evaporation of the solvent afforded the desired product as a colorless oil. Distillation under high vacuum (140° C./1.2 mmHg) afforded the title compound as an oil which crystallized on standing (45.5 g, 92%): mp 70°–72° C.; 1H-NMR (CDCl₃) ∂3.73 (d, J=10 Hz, 2H), 3.52 (m, 1H), 3.12 (m, 2H), 1.88 (m, 1H), 1.76 (m, 1H), 1.19–1.66 (complex m, 2H), 1.46 (s, 9H); CIMS (MH⁺ calcd for $C_{10}H_{19}NO_3$): 202. Found (MH⁺): 202; Anal. (calcd for $C_{10}H_{19}NO_3$): C, H, N.

EXAMPLE 2

1-(tert-Butoxycarbonyl)-3-(methanesulfonyloxy)-piperidine

To a stirred solution of the title compound of Example 1 (44.3 g, 220 mmol) and Et₃N (61.4 mL, 440 mmol, 2 eq) in THF (250 mL) was added dropwise at rt (maintained by cooling from an ice bath), methanesulfonyl chloride (27.77 g, 242 mmol, 1.1 eq). The reaction mixture was stirred for 1 h at rt when TLC (solvent system C) indicated completion. The precipitated Et₃N•HCl was removed by filtration and the filter cake was washed with 50 mL of THF. The combined filtrate and washings were evaporated in vacuo to give the crude product as a yellow oil. This was dissolved in EtOAc/hexanes (1:2) and passed through a pad of silica gel eluting with ethyl acetate/hexanes (1:3). Evaporation of the filtrate afforded the product as a pale yellow oil (59.1 g, 96%) which crystallized on standing. Recrystallization from EtOAc/hexane (1:10) afforded an analytically pure sample: mp 69°–70° C.; 1H-NMR (CDCl₃) ∂4.72 (m, 1H), 3.63 (m, 2H), 3.46 (m, 1H), 3.32 (m, 1H), 3.05 (s, 3H), 1.75–2.06 (complex m, 4H), 1.46 (s, 9H); CIMS (MH⁺ calcd for $C_{11}H_{21}NO_5S$): 280. Found (MH⁺): 280; Anal. (calcd for $C_{11}H_{21}NO_5S$): C, H, N.

EXAMPLE 3

3-Azido-1-(tert-butoxycarbonyl)piperidine

A mixture of the title compound of Example 2 (57.1 g, 205 mmol) and NaN₃ (39.9 g, 614 mmol, 3.0 eq) in DMF (200 mL) was heated and stirred at 70° C. for 48 h when TLC (solvent system C) indicated the reaction to be complete. The reaction mixture was cooled to rt and poured into cold water (200 mL). The aqueous mixture was extracted with Et₂O (500 mL) and the organic extract was back-washed with water (2×100 mL), dried (Na₂SO₄) and the solvent was evaporated in vacuo to afford the product (45.5 g, 98%) as a colorless oil: 1H-NMR (CDCl₃) ∂3.66–3.80 (m, 1H), 3.57 (m, 1H), 3.46 (m, Japp=4.0 Hz, 1H), 3.12 (m, 2H), 1.90–2.05 (m, 2H), 1.69–1.83 (m, 2H), 1.47 (s, 9H). No attempt was made to further purify or characterize this compound.

EXAMPLE 4

3-Amino-1-(tert-butoxycarbonyl)piperidine

A solution of the title compound of Example 3 (37.1 g, 164 mmol) in a mixture of MeOH (100 mL) and acetic acid (25 mL) was added 10% Pd-C (3.7 g) and the reaction mixture was hydrogenated (50. psi) for 24 h at rt in a Parr apparatus. Analysis of the reaction by TLC (solvent system A) and IR (to look for presence or absence of N₃ str peak at 2100 cm$^{-1}$) indicated the reaction to be complete. The solution was filtered through celite to remove catalyst and the filtrate was evaporated in vacuo to give the crude product as an oily residue. The residue was dissolved in 500 mL of 10% aqueous acetic acid and the solution was extracted with Et₂O (3×200 mL). The combined ethereal extract was discarded and the aqueous solution was basified by addition of excess concentrated aqueous NH₃ solution. The basified mixture was extracted with Et₂O (3×200 mL) and the combined organic extract was dried (Na₂SO₄) and evaporated to give the product (22.8 g, 69%) as a pale yellow oil. The hemifumarate of the title compound crystallized from 2-propanol: mp 197°–198° C., 1H-NMR (CDCl₃) ∂3.93 (br s, 1H), 3.82 (dm, $J_{gem}$=13 Hz, 1H), 2.70–2.87 (complex m, 2H), 2.56 (m, 1H), 1.93 (dm, $J_{gem}$=13 Hz, 1H), 1.68 (m, 1H), 1.46 (s, 9H), 1.29–1.41 (complex m, 3H), 1.24 (m, 1H); CIMS (MH⁺ calcd for $C_{10}H_{20}N_2O_2$): 201. Found (MH⁺): 201; Anal. (calc'd for $C_{10}H_{20}N_2O_2 \cdot 0.5 C_4H_4O_4$):C,H,N.

EXAMPLE 5

1-(tert-Butoxycarbonyl)-3-(formamido)piperidine

The title compound of Example 4 (10.1 g, 50.5 mmol) was dissolved in ethyl formate (50 mL) and the solution was refluxed overnight when TLC (solvent system A) showed the reaction to be complete. The solvent was evaporated in vacuo and the residue was dried under high vacuum to give the product (11.5 g, quantitative) as a colorless oil: 1H-NMR (CDCl₃) ∂8.16. (s, 1H), 6.03 (20%), 5.77 (80%) (br s, 1H), 4.06 (m, 1H), 3.22–3.58 (complex m, 4H), 1.20–1.89 (complex m, 4H), 1.46 (s, 9H). CIMS (MH⁺ calcd for $C_{11}H_{20}N_2O_3$): 229. Found (MH⁺): 229; HRMS (M⁺ calcd for $C_{11}H_{20}N_2O_3$): 228. 1474. Found (M⁺): 228. 1469.

EXAMPLE 6

3-(Methylamino)-1-(methyl)piperidine

A solution of the title compound of Example 5 (10.8 g, 47.4 mmol) in THF (20 mL) was added dropwise at rt to a stirred solution of LiAlH₄ in THF (153 mL of a 1.0M solution, 153 mmol, 3.2 eq). The solution was stirred overnight at rt when TLC (solvent system B) indicated incomplete reduction. However, reduction was found to be complete after boiling under reflux for 4 h. The solution was stirred, cooled to 0° C. (ice bath) and treated dropwise with water (5.8 mL), 15% aqueous NaOH (5.8 mL) and finally water (17.4 mL). The mixture was stirred for 1 h and then filtered. Aqueous HCl was added (to pH=1) and the solvent was evaporated in vacuo to give the hydrochloride salt of the product (8.28 g, 87%) as an oil which failed to crystallize. However, the bisfumarate salt crystallized from MeOH: mp 184°–186° C.; 1H-NMR (CDCl₃) ∂2.82 (m, 1H), 2.48–2.68 (complex m, 3H), 2.43 (s, 3H), 2.26 (s,3H), 1.98 (m, 1H), 1.82 (m, 2H), 1.65–1.76 (m, 1H), 1.36–1.65 (complex m, 2H); CIMS (MH$^+$ calcd for $C_7H_{16}N_2$: 129. Found (MH$^+$): 129; Anal. (calcd for $C_{15}H_{24}N_2O_8$): C,H,N.

EXAMPLE 7

3-[N-(3,4-Dichlorophenylacetyl)-N-(methyl)amino]-1-(methyl)piperidine

To a solution of the title compound of Example 6 (3.00 g, 23.4 mmol) and 3,4-dichlorophenylacetic acid (7.21 g, 35.2 mmol, 1.5 eq) in $CH_2Cl_2$ (200 mL) was added DCC (9.67 g, 46.9 mmol, 2 eq) and the reaction mixture was stirred overnight at room temperature. The precipitate was filtered and the filter-cake was washed with ether (50 mL). The combined filtrate and washings were diluted to 500 mL with ether and extracted with 10% aqueous citric acid (200 mL). The citric acid extract was washed further with 2×200 mL ether and the etheral washings were discarded. The aqueous citric acid layer was basified by the addition of excess conc. aqueous ammonia solution, extracted with $CH_2Cl_2$ (200 mL) and the $CH_2Cl_2$ extract was dried ($Na_2SO_4$) and evaporated in vacuo to give a crystalline residue (5.4 g, 73%). Recrystallization from EtOAc/isooctane (1:4) afforded a pure sample: mp 99°–100° C.; $^1$H-NMR (CDCl$_3$) $\partial$7.38 (60%), 7.37 (40%) (d, J=7.8 Hz, 1H), 7.34 (d, J=1.9 Hz, 1H), 7.12 (60% ), 7.09 (40% ), (dd, J=1.9, 7.8 Hz, 1H), 4.58 (40%), 3.82 (60%) (m, 1H), 3.71 (60%), 3.64 (40%), (s, 2H), 2.88 (40% ), 2.84 (60% ) (s, 3H), 2.66–2.86 (m, 2H), 2.27 (60%), 2.26 (40%) (s, 3H), 1.33–2.08 (complex m, 6H); CIMS (MH$^+$ calcd for $C_{15}H_{20}Cl_2N_2O$): 315. Found (MH$^+$): 315; Anal. (calcd for $C_{15}H_{20}Cl_2N_2O$): C, H, N.

EXAMPLE 8

3-[N-[2-(3,4-Dichlorophenyl)ethyl]-N-(methyl)amino]-1-(methyl)piperidine (Compound 1)

The title compound of Example 7 (2.09 g, 6.63 mmol) in THF (20 mL) was added dropwise at r.t. to a 1.0 M solution of AlH$_3$ in THF (33 mL, 5 equiv). TLC (solvent system A) indicated the reaction to be complete after 20 min. The reaction was poured into 15% aqueous NaOH (100 mL) and extracted with CHCl$_3$ (100 mL). The organic layer was separated, dried (Na$_2$SO$_4$) and evaporated in vacuo to give the product (2.0 g, quantitative) as a colorless oil. The fumarate (2-propanol): mp 166°–167° C.; $^1$H-NMR (CDCl$_3$) $\partial$7.34 (d, J=8.1 Hz, 1H), 7.29 (d, J=4.1 Hz, 1H), 7.03 (dd, J=4.1, 8.1 Hz, 1H), 2.89 (dm, J$_{gem}$=11 Hz, 1H), 2.53–2.81 (complex m, 6H), 2.35 (s, 3H), 2.27 (s, 3H), 1.65–1.86 (complex m, 4H), 1.58 (m, 1H), 1.18 (m, 1H); CIMS (MH+ calcd) for $C_{15}H_{22}Cl_2N_2$: 301. Found (MH+): 301; Anal. (calcd or $C_{23}H_{30}Cl_2N_2O_8$): C, H, N.

EXAMPLE 9

1-(tertButoxycarbonyl)-2-piperidinecarboxylic acid

A mixture of pipecolinic acid (48.43 g, 375 mmol), di-tertbutyl dicarbonate (98.2 g, 450 mmol, 1.2 eq) and NaHCO$_3$ (126 g, 1500 mmol, 4.0 eq) in water (1000 mL) was stirred overnight at rt. Crushed ice (200 g) was added to the reaction mixture which was then treated dropwise with a solution of 120 mL of 12M HCl made up to 500 mL with water. The pH was adjusted to ca. 3.5 by addition of a further amount of HCl. The solution was extracted with EtOAc (2×500 mL) and the combined organic extract was back washed with water (2×500 mL) and evaporated in vacuo to give the product (48.7 g, 57%) as a beige crystalline solid: mp 123°–124° C.; $^1$H-NMR (CDCl$_3$) $\partial$4.93 (58%), 4.78 (42%) (m, 1H), 3.96 (m, 1H), 2.96 (m, 1H), 2.22 (m, 1H), 1.68 (complex m, 3H), 1.23–1.50 (m, 2H), 1.46 (s, 9H); CIMS (MH$^+$ calcd for $C_{11}H_{19}NO_4$): 230. Found (MH$^+$): 230; Anal. (calcd for $C_{11}H_{19}NO_4$): C,H,N.

EXAMPLE 10

1-Methyl-2-piperidinemethanol

The title compound of Example 9 (23.2 g, 101 mmol) in dry THF (100 mL) was added dropwise to a 1.0M solution of LiAlH$_4$ in THF (405 mL, 405 mmol, 4eq) and the reaction mixture was refluxed overnight and the product was isolated as described in Example 6 to give the product (13.1 g, quantative) as a colorless oil. The fumarate salt crystallized from 2-propanol: mp 118°–120° C.; $^1$H-NMR (CDCl$_3$) $\partial$3.85 (dd, J=gem=11 Hz, J=3.9 Hz, 1H), 3,39 (dd, J=gem=11 Hz, J=2.2 Hz, 1H), 2.89 (m, 1H), 2.30 (s, 3H), 2.15 (m, 1H), 1.97 (m, 1H), 1.76 (m, 1H), 1.42–1.68 (complex m, 4H), 1.28 (m, 1H); CIMS (MH$^+$ calcd for $C_7H_{15}NO$): 130. Found (MH$^+$): 130; Anal. ($C_{11}H_{19}NO_5$): C,H,N.

EXAMPLE 11

1-Methyl-2-(methylaminomethyl)piperidine

Method A.

To a stirred solution of MeSO$_2$Cl (7.81 g, 68.2 mmol, 1.1 eq) in hydrocarbon stabilized CHCl$_3$ (100 mL) was added, dropwise at rt, a solution of the title compound of Example 10 (8.00 g, 62 mmol) in CHCl$_3$ (25 mL). The reaction mixture was stirred at rt until complete by TLC (solvent system B) and the solvent was evaporated in vacuo. The residue was dissolved in water (100 mL) and added dropwise to a stirred solution of MeNH$_2$ in water (420 mL of a 40% solution). The reaction mixture was stirred overnight at rt, cooled (ice) and then treated with NaOH (120 g). The basified solution was extracted with CHCl$_3$ (2×200 mL) and the combined organic extract was evaporated in vacuo to give the desired product (8.8 g, quantitative). The oxalate salt crystallized from MeOH: mp 177.5°–178° C.; $^1$H-NMR (CDCl$_3$): a 2.84 (m, 1H), 2.66 (d, J=4.4 Hz, 2H), 2.44 (s, 3H), 2.26 (s, 3H), 2.09 (m, 1H), 1.96 (m, 1H), 1.39–1.79 (m, 4H), 1.26 (m, 2H); CIMS (MH$^+$ calcd for $C_8H_{18}N_2$): 143. Found (MH$^+$): 143; Anal. (calcd for $C_{12}H_{22}N_2O_8$): C,H,N.

Method B.

A solution of N-t-Boc-N'-methylpipecolinamide (prepared as in Example 12) (1.0 g, 4.1 mmol) in THF (10 mL) was added dropwise to a 1M solution of AlH$_3$ in THF (21 mL, 21 mmol, 5 eq) at room temperature. The reaction mixture was treated as described in Example 8 to give the desired product which was identical to that described above in Method A. The oxalate salt crystallized from MeOH as above in Method A (0.68 g, 71%): mp 177.5°–178° C.; $^1$H-NMR (CDCl$_3$) identical to material obtained via Method A above.

EXAMPLE 12

1-(tertButoxycarbonyl) -N-methylpipecolinamide

N-t-Boc-pipecolinic acid prepared as in Example 9 (3 g, 13.1 mmol) was dissolved in CHCl$_3$ (30 mL) and Et$_3$N (1.9 mL) was added. The solution was cooled down to −10° C. (ice-salt bath) and isobutyl chloroformate (1.8 g, 13.1 mmol, 1 eq) was added. The reaction was stirred at −10° C. for 30–45 min and then MeNH$_2$ (gas) was bubbled through the reaction mixture for 2 hours. The organic layer was washed with brine (3×100 mL), ice-cooled 10% citric acid solution (2×70 mL), satd NaHCO$_3$ (1×50 mL) and finally brine (2×50 mL). The solvent was removed in vacuo to give analytically pure product as a colorless crystalline solid (5.1 g, quantitative yield) mp: 83°–83.5° C.; $^1$H-NMR (CDCl$_3$) ∂6.07 (br s, 1H, NH), 4.73 (m, 1H), 4.04 (m, 2H), 2.84 (50%), 2.82 (50%) (s, 3H, NHMe), 2.67–2.85 (m, 1H, CH$_2$N), 2.33 (m, 1H, CH2N), 1.25–1.75 (complex m, 4H), 1.48 (s, 9H); CIMS (MH$^+$ calc for C$_{12}$H$_{22}$N$_2$O$_3$): 243. Found (MH$^+$): 243; Anal. (calcd for C$_{12}$H$_{22}$N$_2$O$_3$):C, H, N.

EXAMPLE 13

2-[N-(3,4-Dichlorophenylacetyl)-N-(methyl)-aminomethyl]-1-(methyl)piperidine The base obtained from the oxalate salt of the title compound of Example 11 (3.5 g, 15.1 mmol) and 3,4-dichlorophenylacetic acid (4.64 g, 22.6 mmol, 1.5 eq) was coupled in CH$_2$Cl$_2$ in the presence of DCC (6.22 g, 30.2 mmol, 2 eq) as described in Example 7 to give the desired product (3.1 g, 62% ) as a colorless oil which failed to form any crystalline salts: $^1$H-NMR (CDCl$_3$) ∂7.33–7.41 (m, 2H), 7.10 (dd, J=2.1, 8.2 Hz, 1H), 3.86 (dd, J$_{gem}$=13 Hz, J=4.4 Hz, 1H), 3.67 (dd, J$_{gem}$=13 Hz, J=2.7 Hz, 1H), 3.65 (s, 2H), 3.11–3.29 (m, 1H), 3.05 (63%), 2.96 (37%) (s, 3H), 2.84 (m, 1H), 2.33 (63%), 2.31 (37%) (2, 3H), 2.07–2.34 (m, 2H), 1.15–1.84 (complex m, 5H); CIMS (MH$^+$ calcd for C$_{16}$H$_{22}$Cl$_2$N$_2$O): 329. Found (MH+): 329; HRMS (M$^+$ calcd for C$_{16}$H$_{22}$Cl$_2$N$_2$O): 328.1109. Found (M$^+$): 328.1117.

EXAMPLE 14

(Compound 2)

2-[N-[2-(3,4-Dichlorophenyl)ethyl]-N-(methyl)-aminomethyl]-1-(methyl)piperidine The title compound of Example 13 (2.00 g, 6.08 mmol) was reduced with 1.0M AlH$_3$ in THF (30 mL, 30 mmol, 5 eq) as described in Example 8 to give the desired product (1.91 g, quantitative) as a colorless oil. This product failed to form any crystalline salts even after rigorous purification of the base. The crude reaction product was further purified by column chromatography eluting with CHCl$_3$/MeOH/conc. aq NH$_3$ (solvent system A) prior to submission for biological testing. $^1$H-NMR (CDCl$_3$) ∂7.33 (d, J=8.1 Hz, 1H), 7.30 (d, J=2.0 Hz, 1H), 7.03 (dd, J=2.0, 8.1 Hz, 1H), 2.82 (m, 1H), 2.69 (d, J=7.5 Hz, 2H), 2.49–2.66 (m, 3H), 2.28 (s, 3H), 2.25 (° s, 3H), 2.16–2.25 (m, 1H), 2.08 (m, 1H), 1.94 (m, 1H), 1.64–1.81 (m, 2H), 1.49–1.81 (m, 2H), 1.09–1.30 (m, 2H); CIMS (MH$^+$ calcd for C$_{16}$H$_{24}$Cl$_2$N$_2$): 315. Found (MH$^+$): 315; HRMS (M$^+$ calcd for C$_{16}$H$_{24}$Cl$_2$N$_2$): 314.1316. Found (M$^+$0): 314.1322.

EXAMPLE 15

2-(3,4-Dichlorophenylacetamidomethyl)-1-(ethyl)pyrrolidine

2-Aminomethyl-1-(ethyl)pyrrolidine (Aldrich) (3.2 g, 25 mmol) and 3,4-dichlorophenylacetic acid (7.7 g, 37.6 mmol, 1.5 eq) were coupled in CH$_2$Cl$_2$ in the presence of DCC (10.6 g, 51 mmol, 2 eq) as described in Example 7 to give the desired product (7.6 g, 97%) as a colorless oil: $^1$H-NMR (CDCl$_3$) ∂7.41 (d, J=8.2 Hz, 1H), 7.39 (d, J=2.0 Hz, 1H), 7.13 (dd, J=2.0, 8.2 Hz, 1H), 6.13 (br s, 1H), 3.51 (s, 2H), 3.37 (m, 1H), 3.07 (m, 2H), 2.65 (m, 1H), 2.53 (m, 1H), 2.04–2.21 (m, 2H, CH$_2$CH$_3$ ), 1.81 (m, 1H), 1.67 (m, 1H), 1.35–1.60 (complex m, 2H), 0.99 (t, J=7.2 Hz, 3H); CIMS (MH$^+$ calcd for C$_{15}$H$_{20}$Cl$_2$N$_2$O): 315. Found (MH$^+$): 315; Anal. (calcd for C$_{15}$H$_{20}$Cl$_2$N$_2$O): C,H,N.

EXAMPLE 16

(Compound 3)

2-[N-(3,4-dichlorophenylethyl)aminomethyl]-1-(ethyl)pyrrolidine

The title compound of Example 15 (base) (6.39 g, 20.3 mmol) was reduced with a 1.0M solution of AlH$_3$ in THF (60 mL, 60 mmol, 3 eq) as described in Example 8 to give the crude product as a colorless oil (6.1 g, quantitative). The oxalate salt (6.5 g, 80% ) crystallized from 2-propanol/MeOH (1:1): mp 181°–182° C. (dec); $^1$H-NMR (CDCl$_3$) ∂7.35 (d, J=8.1 Hz, 1H), 7.31 (d, J=1.8 Hz, 1H), 7.05 (dd, J=1.8, 8.1 Hz, 1H), 3.14 (m, 1H), 2.80–2.91 (m, 2H), 2.67–2.80 (complex m, 4H), 2.58 (m, 1H), 2.48 (m, 1H), 2.24 (m, 1H), 2.15 (q, J=8.6 Hz, 1H), 1.89 (m, 1H), 1.73 (m, 2H), 1.60 (m, 2H° ), 1.07 (t, J=8.6 Hz, 3H); CIMS (MH$^+$ calcd for C$_{15}$H$_{22}$Cl$_2$N$_2$): 301. Found (MH$^+$): 301; Anal. (calcd for C$_{17}$H$_{24}$Cl$_2$N$_2$O•0.5H$_2$O): C,H,N.

EXAMPLE 17

2-(3,4-Dichlorophenylethylformamidomethyl)-1-(ethyl)pyrrolidine

A solution of the title compound of Example 16 (1.2 g, 3.99 mmol) in EtOCHO (50 mL) containing 6 drops of formic acid was boiled under reflux overnight when TLC (solvent system A) indicated the reaction to be complete. The solvent was evaporated in vacuo and the residue was partitioned between excess dilute aqueous NH$_3$ (50 mL) and CHCl$_3$ (50 mL). The CHCl$_3$ layer was separated, dried (Na$_2$SO$_4$) and evaporated in vacuo to give the product as an oil (1.31 g, quantitative). Two rotamers were visible on TLC solvent system A: $^1$H-NMR for major 80% rotamer (CDCl$_3$) ∂8.39 (s, 1H), 7.38 (d, J=8.2 Hz, 1H), 7.28 (d, J=2.0 Hz, 1H), 7.00 (dd, J=2.0, 8.2 Hz, 1H), 3.95 (dd, Jgem=13 Hz, J=4.7 Hz, 1H), 3.28–3.86 (complex m, 6H), 2.77–2.98 (complex m, 4H), 2.15 (m, 1H), 1.84–2.09 (complex m, 3H), 1.37 (t, J+7.2 Hz, 3H); CIMS (MH$^+$ calcd for C$_{16}$H$_{22}$Cl$_2$N$_2$O): 329. Found (MH$^+$): 329. No attempt was made to further purify this material.

EXAMPLE 18

(Compound 4)

2-[N-(3,4-Dichlorophenylethyl)-N-(methyl)-aminomethyl]-1-(ethyl)pyrrolidine

The title compound of Example 17 (0.82 g, 2.49 mmol) was reduced with a 1.0M solution of AlH$_3$ in THF (10 mL, 10 mmol, 4 eq) as described in Example 8 to give the crude product as a colorless oil. The oxalate salt (1.18 g, 96%) crystallized from 2-propanol: mp 172°–173° C.; $^1$H-NMR (CDCl$_3$) ∂7.33 (d, J=8.1 Hz, 1H), 7.29 (d, J=2.0 Hz, 1H), 7.03 (dd, J=2.0, 8.1 Hz, 1H), 3.17 (m, 1H), 2.92 (m, 1H) 2.32–2.76 (complex m, 8H), 2.28 (s, 3H), 2.20 (m, 1H), 2.11 (q, J=8.1 Hz, 1H), 1.84–1.98 (m, 1H), 1.51–1.83 (m, 2H), 1.09 (t, J=8.1 Hz, 3H); CIMS (MH$^+$ calcd for C$_{16}$H$_{24}$Cl$_2$N$_2$): 315. Found (MH$^+$): 315; Anal. (calcd for C$_{20}$H$_{28}$Cl$_2$N$_2$O$_8$): C,H,N.

Biological Evaluation

Radioreceptor Assay

The compounds of Examples 8, 14, 16 and 18 were tested for their ability to displace [$^3$H](+)-pentazocine from guinea pig brain membranes [de Costa et al, FEBS Lett., 251, 53–58, 1989] to determine the relative potency of the compounds interacting with the; sigma receptor. Receptor binding assays were performed using the crude synaptosomal (P$_2$) membrane fraction of guinea pig brain.

Crude P$_2$ membrane fractions were prepared from frozen (−80° C.) guinea pig brains (Pel-Freeze, Rogers, AK), minus cerebella. After removal of cerebella, brains were allowed to thaw slowly on ice and placed in ice-cold 10 mM Tris-HCl, pH 7.4, containing 320 mM sucrose (Tris-sucrose buffer). Brains were then homogenized in a Potter-Elvehjem homogenizer by 10 strokes of a motor driven Teflon pestle in a volume of 10 mL/g tissue wet weight. The homogenate was centrifuged at 1000g for 10 min at 4° C., and the supernatants were saved. The pellets were resuspended by vortexing in 2 mL/g ice-cold Tris-sucrose and centrifuged again at 1000g for 10 min. The combined 1000 g supernatant was centrifuged at 31000 g for 15 min at 4° C. The pellets were resuspended by vortexing in 3 mL/gm of 10 mM Tris-HCl, pH 7.4, and the suspension was allowed to incubate at 25° C. for 15 min. Following centrifugation at 31000 g for 15 min, the pellets were resuspended by gentle Potter-Elvehjem homogenization to a final volume of 1.53 mn/g in 10 mM Tris-HCl, pH 7.4. Aliquots were stored at −80° C. until use. Protein concentration was determined by the method of Lowry et al. [Lowry et al, J. Biol. Chem., 193, 265–271, 1951] using bovine serum albumin (BSA) as standard.

To prepare rat brain crude P$_2$ membranes, male Sprague-Dawley rats (150–200 g, Charles River, Boston, Mass.) were sacrificed by decapitation. Brains (minus cerebella) were then treated as described above.

Each compound was initially screened at concentrations of 10, 100, and 1000 nM in order to obtain an estimate of sigma binding affinity and to determine the appropriate concentration range to use in 12-point competition curves. For most compounds in the study, a concentration range of 0.0005–100 nM was appropriate. A range of 0.005–1000 nM or 0.05–10,000 nM was used for the less potent compounds. Twelve concentrations of unlabeled ligand were incubated with 3 nM [$^3$H](+)-pentazocine as described previously [de Costa et al, FEBS Lett., 251, 53–58, 1989]. The CDATA iterative curve-fitting program (EMF Software, Inc., Baltimore, Md.) was used to determine IC$_{50}$ values. Values are the average of 2–4 experiments ±SEM. Each experiment was carried out in duplicate. The Cheng-Prussoff equation [Cheng, Y. C. and Prusoff, W. H., Biochem. Pharmacol, 22, 3099–3108, 1973 was then used to convert IC$_{50}$ values to apparent K$_i$ values. The Kd for [$^3$H]-(+)-pentazocine (4.8 nM) was determined in independent experiments using guinea pig brain membranes.

Sigma receptors were labeled with [$^3$H]-(+)-pentazocine (Specific activity =51.7 Ci/mmol). Incubations were carried out in 50 mM Tris-HCl, pH 8.0, for 120 min at 25° C. in a volume of 0.5 mL with 500 µg of membrane protein and 3 nM [$^3$H]-(+)-pentazocine. Nonspecific binding was determined in the presence of 10 µM (+)-pentazocine. Assays were terminated by the addition of 5 mL of ice-cold 10 mM Tris-HCl, pH 8.0, and filtration through glass-fiber filters (Schleicher and Schuell). Filters were then washed twice with 5 mL of ice-cold Tris-HCl buffer. Filters were soaked in 0.5% polyethylenimine for at least 30 min at 25° C. prior to use.

TABLE I

| Test Compound | Ki([3H](+)-Pent) (nM) + SEM |
|---|---|
| Compound 1 | 2.30 ± 0.13 |
| Compound 2 | 3.69 ± 0.85 |
| Compound 3 | 16.05 ± 3.62 |
| Compound 4 | 1.48 ± 0.37 |
| DTG | 27.7 ± 4.3 |
| (+) Pentazocine | 3.1 ± 0.3 |
| Haloperidol | 3.7 ± 0.6 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical o compositions may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However,.a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, aqueous sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound represented by the following formula:

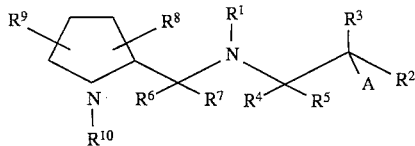

wherein
each of $R^1$ and $R^{10}$ is independently selected from the group consisting of hydrido, alkyl, cycloalkyl, hydroxyalkyl, haloalkyl, cycloalkylalkyl, alkoxyalkyl, aralkyl, aryl, alkenylalkyl, alkynylalkyl, carboxyalkyl, alkanoyl, alkylsulfinyl, alkylsulfonyl, arylsulfinyl and arylsulfonyl;

each of $R^2$ and $R^3$ is independently selected from the group consisting of hydrido, alkyl, cycloalkyl, hydroxyalkyl, haloalkyl, cycloalkylalkyl, alkoxyalkyl, aralkyl, aryl, alkenyl, alkynyl, alkenylalkyl, alkynylalkyl, carboxyalkyl, alkanoyl, alkoxycarbonyl, carboxy, cyanoalkyl, alkylsulfinyl, alkylsulfonyl, arylsulfinyl, and arylsulfonyl;

or $R^2$ and $R^3$ may be taken together to form oxo;

each of $R^4$ through $R^9$ is independently selected from hydrido, alkyl, cycloalkyl, cycloalkylalkyl, aralkyl, aryl, alkoxyalkyl, haloalkyl, hydroxyalkyl, carboxy, carboxyalkyl, alkanoyl, alkenyl and alkynyl;

or $R^6$ and $R^7$ may be taken together to form oxo;

or $R^8$ and $R^9$ may be taken together to form oxo;

A is selected from the group consisting of phenyl or napthyl which can be further substituted with one or more substitutents independently selected from the group consisting of hydrido, hydroxy, alkyl, cycloalkyl, cycloalkylalkyl, aralkyl, aryl, alkoxy, aryloxy, aralkoxy, alkoxyalkyl, halo, haloalkyl, hydroxyalkyl, cyano, amino, monoalkylamino, dialkylamino, carboxy, carboxyalkyl, alkanoyl, alkenyl and alkynyl; or a pharmaceutically acceptable salt thereof.

2. A compound of claim 1, wherein each of $R^1$ through $R^{10}$ is independently selected from hydrido or alkyl, and A is phenyl which is substituted with one or more substituents selected from hydrido, hydroxy, alkyl, alkoxy, alkoxyalkyl, halo and haloalkyl.

3. A compound of claim 1, wherein each of $R^1$ and $R^{10}$ is selected from hydrido or alkyl; wherein each of $R^2$ through $R^9$ is hydrido, and A is phenyl substituted with one or more substituents selected from hydrido and halo.

4. A compound of claim 3, wherein $R^1$ is hydrido or methyl, $R^{10}$ is ethyl, and halo is chloro.

5. A compound of claim 1, which is 2-[N-(3,4-dichlorophenylethyl)aminomethyl]-1-(ethyl)pyrrolidine.

6. A compound of claim 1, which is 2-[N-(3,4-dichlorophenylethyl)-N-(methyl)aminomethyl]-1-(ethyl)pyrrolidine.

7. A pharmaceutical composition comprising a compound of claim 1.

8. A pharmaceutical composition comprising a compound of claim 5.

9. A pharmaceutical composition comprising a compound of claim 6.

10. A method for treating a patient afflicted with or susceptible to Cerebral ischemia, which method comprises administering to the patient a therapeutically-effective amount of a compound of claim 1.

11. A method for treating a patient afflicted with or susceptible to Cerebral ischemia, which method comprises administering to the patient a therapeutically-effective amount of a compound of claim 5.

12. A method for treating a patient afflicted with or susceptible to Cerebral ischemia, which method comprises administering to the patient a therapeutically-effective amount of a compound of claim 6.

* * * * *